United States Patent [19]
Swenson

[11] Patent Number: 5,831,182
[45] Date of Patent: Nov. 3, 1998

[54] REMOTE SAMPLING DEVICE FOR DETERMINING AIR BORNE BACTERIA CONTAMINATION LEVELS IN CONTROLLED ENVIRONMENTS

[76] Inventor: Erik A. Swenson, 2232 Blue Bird Dr., Longmont, Colo. 80501

[21] Appl. No.: 961,761

[22] Filed: Oct. 31, 1997

[51] Int. Cl.[6] .................................................. G01N 1/22
[52] U.S. Cl. ....................................................... 73/863.22
[58] Field of Search ........................... 73/863.21, 863.22, 73/28.01, 28.04, 28.05; 55/270; 435/30

[56] References Cited

U.S. PATENT DOCUMENTS

| | | |
|---|---|---|
| 2,894,877 | 7/1959 | Sinden . |
| 3,001,914 | 9/1961 | Anderson . |
| 3,475,951 | 11/1969 | Goetz ..................................... 73/28.01 |
| 3,518,815 | 7/1970 | McFarland et al. .................. 73/863.22 |
| 3,968,012 | 7/1976 | Jones . |
| 3,972,226 | 8/1976 | Rountree . |
| 4,725,294 | 2/1988 | Berger ................................. 73/863.22 |
| 5,201,231 | 4/1993 | Smith ................................... 73/863.22 |
| 5,421,214 | 6/1995 | Burgdorfer . |
| 5,693,895 | 12/1997 | Baxter ....................................... 55/270 |

OTHER PUBLICATIONS

"Sampling Microbiological Aerosols", Public Health Monograph No. 60, Apr. 1959, Pages/Sampler: 20 & 36/Fort Detrick Slit, 20 & 35/TDL, 21 & 37 Fort Detrick Slit–Incubator, 21 & 38/Casella (Slit).
"Air Sampling Instruments For Evaluation of Atmospheric Contaminants" Publisher: American Conference of Governmental Industrial Hygienists Cincinnati, Ohio 6th Edition–1983, p. Q–11/Casella Airborne Bacteria Sampler MK II Models Large/Small.
5th Edition–178, Pages/Sampler: O–12, O–13/Casella Bacteria Sampler, O–16, O–17/New Brunswick Scientific Models Sta–101, STA–121, STA–203, STA–303.
2nd Edition–1962, Pages/Sampler: B–3–14, B–3–15/Casella Slit Sampler For Airborne Bacteria.

*Primary Examiner*—Robert Raevis

[57] ABSTRACT

A remote slit impact air sampler for recovering viable air borne organisms from a known volume of ambient air. The remote sampler is employed with a sealed sample chamber within which a test plate upon a turntable is rotated beneath a slit type sample inlet. During operation, air passing through the sample slit is accelerated to a velocity that insures impingement of particulate matter from the sampled air volume onto the surface of a nutrient growth medium located within the test plate. Particulate matter and associated bacterial organisms within the sampled air volume are retained upon the surface of the test plate while the sampled air volume is evacuated from the sample chamber through an air outlet, and is then exhausted away from the critical environment at the controller means. Following sampling, the test plate is incubated for a predetermined period of time following which bacterial colony forming units may be quantified. As the volume of air sampled per period of time is known, the density of bacterial organisms per volume of air can then be determined. Moreover, as the rotational speed of the turntable is known, the time of organismal capture may also be determined. The remote sampler is employed with streamline structure allowing it to be placed and operated in a variety of controlled environments, while having negligible disruptive effects on laminar airflow or operations performed therein. Also, the base, below the sealed sample chamber, housing turntable elevation and rotational means, is employed with means to seal its interior from the external environment in a substantially air tight manner, whereby disallowing contaminant ingress and egress which might jeopardize the environment in which it is utilized. Further, the device is constructed of substantially non-particulate shedding or harboring materials that allow for complete routine chemical sanitization with negligible degradation. Additionally, the device utilizes standard 100 mm test plates to greatly reduce the cost of operation.

9 Claims, 8 Drawing Sheets

REMOTE SAMPLING DEVICE FOR DETERMINING AIR BORNE BACTERIA CONTAMINATION LEVELS IN CONTROLLED ENVIRONMENTS

BACKGROUND OF THE INVENTION

1. Field of the Invention

The present invention relates in general to an apparatus for the measurement of the amount of airborne contamination. In particular, the present invention relates to an improved device for use in environments such as pharmaceutical or medical clean rooms which will impact air upon a microbial growth medium, such that the growth medium may be cultured to determine the presence of airborne microbial particles within such clean room environments.

2. Description of the Prior Art

A number of different types of devices have been developed to measure biological contamination of ambient air in controlled environments such as Class 100 to 100,000 clean rooms. Some of the more common types of these biological air samplers employ a variety of means in which to impact particulate matter, contained within the sampled volume of air, and thus any viable organisms associated with it onto a variety of test mediums. Following testing with these methods, the quantity and types of viable organisms in air borne particles can be determined by standard bacteriological methods. For example, where the viable particles are deposited on an agar surface, the bacterial colonies can be incubated on the medium and can be counted and identified under a microscope or by using a variety of identification systems.

The most successful types of biological air samplers have been the slit impact or slit-to-agar (STA) biological air samplers. The slit impact sampler has received wide recognition in the field of medicine, research and industry for the analysis of contamination levels of ambient air environments and has been in regular use to determine air quality in a variety of controlled environments for decades. Several models of these slit impact samplers have been developed and described over the years. These samplers include the Fort Detrick Slit Sampler (described in *Sampling Microbiological Aerosols*, Public Health Monograph No. 60, at 36); the Slit-to-Agar (STA) Air Sampler from Barramundi Corporation of Homosassa, Fla.; the STA Sampler from New Brunswick (described in *Air-Sampling Instruments for Evaluation of Atmospheric Contaminants,* 5th Edition (1978), American Conference on Governmental Industrial Hygienics (pp. 0–16)); and the Casella Slit Sampler (described in Public Health Monograph, No. 60, at 38).

The slit impact sampler utilizes a revolving agar plate under a slit-type orifice in a sealed sample chamber to impinge the air sample directly and immediately upon a nutrient collecting medium of solidified agar. Air passing through the slit-type orifice is accelerated to a velocity that insures impingement of particulate matter from the sampled air volume onto the test media. Viable particles immediately find nutrients suitable for their growth in the collection medium, and the sampled air volume then leaves the chamber through an opening in the base or sidewall of the sample chamber. Incubation of the agar collecting plate permits colonies to be counted, speciated and evaluated.

The air sample is drawn through the slit-type orifice by means of a vacuum pump or suitable house vacuum (depending on the model). Rotation of the test plate on a rotating platform within the sealed sample chamber, under the slit-type orifice, by means such as an electric motor, or clock mechanism as described in U.S. Pat. No. 3,972,226, has several crucial functions. Rotation of the test plate assures uniform particle distribution over the surface of the collecting medium, allows for lengthy sample periods which may exceed 60-minutes with some devices, allows for more accurate enumeration of organisms recovered as they are not as readily impacted atop one another, removes the recovered organisms from the direct influx of sampled air thus minimizing loss of organisms captured due to desiccation, and allows for determination of the time of organismal recovery which can then be linked with operations that occurred during that time period.

Although prior art slit impact samplers have been the standard to which other air viable samplers are compared, and offer many advantages over other methods of bacteriological air sampling, several serious deficiencies with these samplers exist. The prior art in slit impact samplers have been designed extremely well for organismal recovery purposes, but have not been designed appropriately for employment in controlled environments. As such, their physical presence and operation imparts a very negative impact on controlled environments in which they are utilized. This impact is discussed in the following text.

Foremost, the cumbersome size of the slit impact sampler imparts a great burden on controlled environments and operations performed therein. As components such as vacuum pumps, electronics, vacuum plumbing and control means are housed in the base, below the sample chamber, the size of the base can be very substantial. Additionally, the standard sample collection plate utilized by these sampler is 150 mm in diameter. As the slit impact samplers are designed to incorporate this oversized and costly test media, the sample chambers of these units are extremely cumbersome as well. Collectively, the slit impact samplers are of considerable proportion, with typical dimensions of the slit impact sampler being roughly 305 mm in width (or depth), 305 mm in height, and 230 mm depth (or width). One unit being as large as 508 mm in width, 457 mm in depth and 1,041 mm in overall height. As such, these devices are much too obtrusive to be employed for air sampling in controlled environments such as laminar airflow hoods or along pharmaceutical fill lines, where the available work space for placement of additional equipment is generally very minimal. Finding and/or creating available work space for placement of these bulky prior art devices, within controlled environments, can be costly and burdensome, and if utilized, may greatly hinder operations performed therein.

Additionally, slit impact samplers can have a very deleterious effect on laminar or unidirectional airflow in controlled environments. Laminar air flow, originating from High Efficiency Particle Air (HEPA) Filters, is intended to bathe controlled environments with a continual shower of contaminant free air. Any obstruction and/or disruption in this laminar air flow can cause turbulence which may introduce air and associated contaminants from downstream, into the controlled environment, where it may jeopardize processing, products, patients, or test materials. The physical presence and operation of prior art slit impact samplers cause a great deal of turbulence within the laminar air flow of controlled environments. This due to the obstruction caused by the substantial size and shape of the samplers and also due to disruption caused by discharge of the sampled air volume from the samplers.

Furthermore, prior art slit impact samplers are very difficult, if not impossible, to completely sanitize. Initially, as the exterior of the devices possess a great deal of surface area, a great deal of time is required to sanitize the device.

Further, as the interior of the base of these devices, below the air tight sampling chamber, is not substantially sealed and as such is open to the environment, contaminants are allowed to enter and be harbored within. Visible particulate matter is commonly present within the interior of these bases and sampling of the interior of these bases for viable organisms has shown recovery of bacteria as well. This viable and non-viable particulate matter, which may be accumulated within the base interior during handling and transport outside of a controlled environment, is often shed within the controlled environments in which these devices are utilized for air quality monitoring. These contaminants may then jeopardize processing, products, surgeries or other aseptic manipulations performed therein.

Sanitization of the interior of the base and the components therein would be a very time and labor intensive procedure and as such a great burden on operators. Additionally, complete sanitization of the base interior would not likely be attained as numerous surfaces exposed to the environment may still not be accessible for sanitization. Also, entrance into the base interior for sanitization would likely invalidate the calibration status of the unit making this procedure very impractical. In addition, crucial components such as the dome, dome seal, and sample inlet and slit orifice assemblies, in most instances may only be chemically sanitized, as opposed to being steam sterilized, due to their composition and/or construction. This may leave undesired bacterial contaminants on these components, obtained from handling and/or previous air quality testing, which may be deposited on the test plate during test sessions performed thereafter, giving an inaccurate assessment of air quality.

To purportedly overcome the reasonable concerns associated with placing these prior art slit impact samplers directly into controlled environments, remote sampling systems have been developed. These remote sampling systems are generally a length of flexible tubing connected to the top of the sampling inlet which leads into the slit orifice of the sampler. With these remote sampling systems the slit impact sampler is placed outside of the controlled environment to be monitored and then the attached remote sampling tube is placed into the controlled environment to be monitored. Air is then drawn from the controlled environment through the tubing into the sample inlet and slit orifice of the slit impact sampler outside of the controlled environment where it is impacted on the test plate as previously described. The drawback with this method is that overall recovery rates of organisms from controlled environments monitored by this means is far from acceptable. Recovery rates may only be 5 to 50% of that which would be recovered by the unit directly, giving a poor indication of the microbial load in the air of the environments monitored. This poor recovery is likely due to static charge and sidewall forces of the tubing acting on particulate matter and organisms associated with it. As such, organisms drawn into the tubing may be detained, desiccated, or otherwise stressed and thus be made non-viable prior to their capture on the test media, if they make it through the tubing at all.

Additionally, components of the sample chambers of many of these prior art slit impact samplers are not sealed in a substantially air tight manner. Inadequate sealing of the sample chamber to the base structure or the sample conduit to the sample chamber may allow a portion of the sampled air volume to enter the sample chamber without passing through the slit inlet. As such, bacterial contaminates associated with this air volume are not captured on the test plate. Therefore, an accurate bacteriological assessment of the air quality is not possible.

OBJECT OF THE PRESENT INVENTION

The object of the present invention is to provide a device for testing air for microorganism content with all the inherent advantages of the prior art in slit impact air samplers, meaning that: the device offer the recognized organismal recovery ability of the slit impact air sampling methodology; the device offer a lengthy sample period which will minimize the number of manipulations required within the controlled environment; the device is powered by an in house power source minimizing the burden on operators (e.g., no batteries to charge, change and monitor); the device distributes the sampled air volume evenly over the test plate surface allowing for easy enumeration of organisms recovered; the device removes organisms captured on the test plate surface from the direct path of incoming sampled air, preventing their desiccation; and the device allows for the determination of the time of bacterial recovery.

But, in addition, the further object of the present invention is to provide a device which offers the following crucial advantages: all components of the device that are exposed to the environment may be easily and completely sanitized, as monitoring of a controlled environment should not introduce additional contaminants into that environment; the interior cavity of the base of the device, under the sample chamber, is sealed in a substantially air tight manner from the external environment in such a manner that disallows contaminants to enter, be harbored, and then shed from its interior surfaces which may not be routinely sanitized; the device is of a streamline size and shape that allows the device to be readily placed in controlled environments which may have minimal available work space, such as along pharmaceutical fill lines or within laminar airflow benches, so as not to be an hindrance to operations performed therein; the device is of a streamline size and shape that would have minimal disruptive affects on laminar air flow within a controlled environment so as not to jeopardize the integrity of that environment; the device utilizes readily available and inexpensive standard 100 mm test plates as to minimize its size and operating cost; the device operates remotely from operative controller means, whereby operative controller means supplying vacuum and power to the device may be located outside the controlled environment greatly minimizing impact on controlled environments in which it is employed; the device employs a substantially air tight seal between critical components of the sample chamber, whereby the only entrance point into the sample chamber is the slit inlet, whereby the sample air volume has to be impacted upon the test plate, as to assure an accurate assessment of the air quality. These and other objects are achieved by a remote sampling device for determining airborne bacteria contamination levels in controlled environments which is described in detail in the following text.

BRIEF DESCRIPTION OF THE DRAWING FIGURES

A more complete appreciation of the remote sampler and many of the attendant advantages thereof will be readily obtained as the same become better understood by reference to the following detailed description when considered in connection with the accompanying drawings, wherein.

Figure 7A:
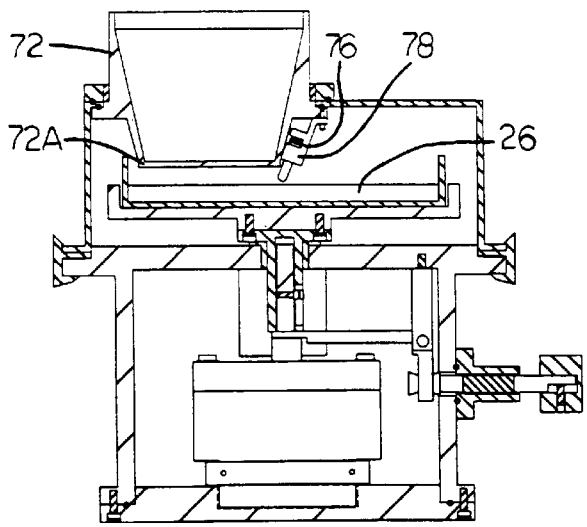
Figure 7B:
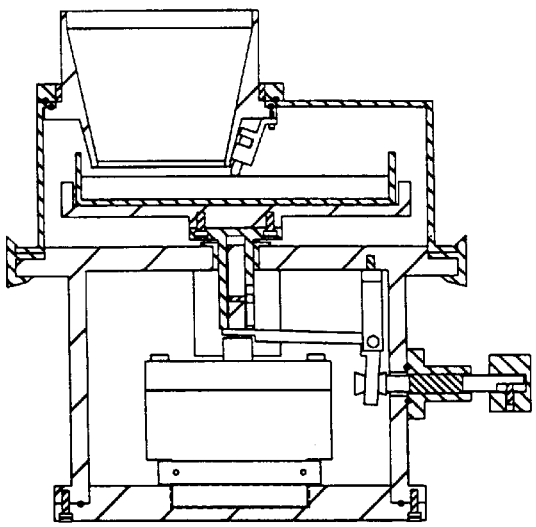
Figure 7C:
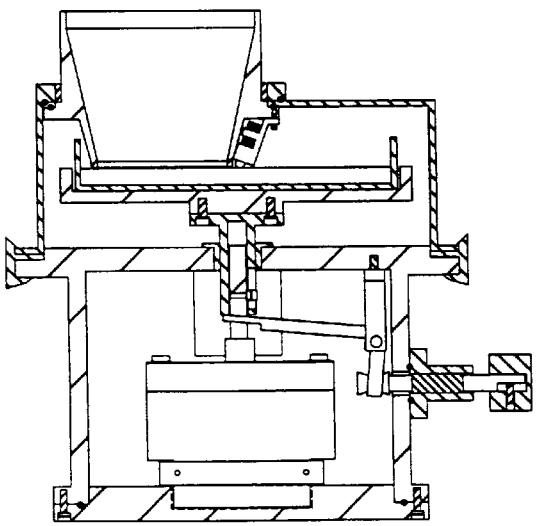

FIGS. 7A, 7B, and 7C are sectional views of the remote sampler showing proper and improper adjustment of the turntable adjustment assembly in conjunction with a distance indicator.

DETAILED DESCRIPTION OF THE DRAWING FIGURES

Figure 1:
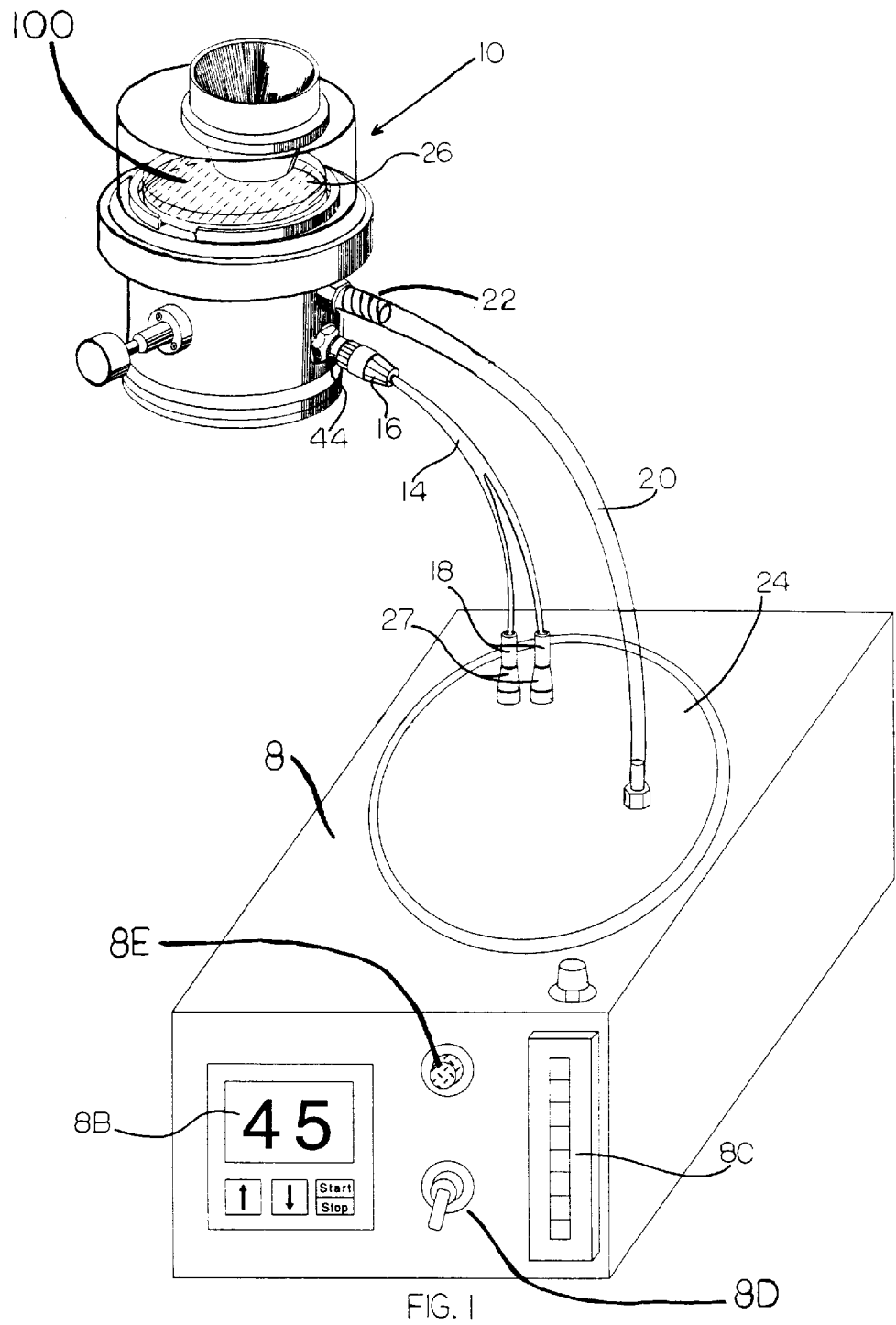
FIG. 1 is an example of the remote sampler as connected to a controller means for sampling.

As depicted in FIG. 1, a remote sampler according to the present invention is generally designated by reference numeral 10. The remote sampler is approximately 130 mm in overall height and approximately 130 mm at its greatest diameter. These dimensions are not intended to limit the scope of the remote sampler but are intended to better illustrate the minuteness of the unit when compared with the prior art in slit impact air samplers.

Figure 2:
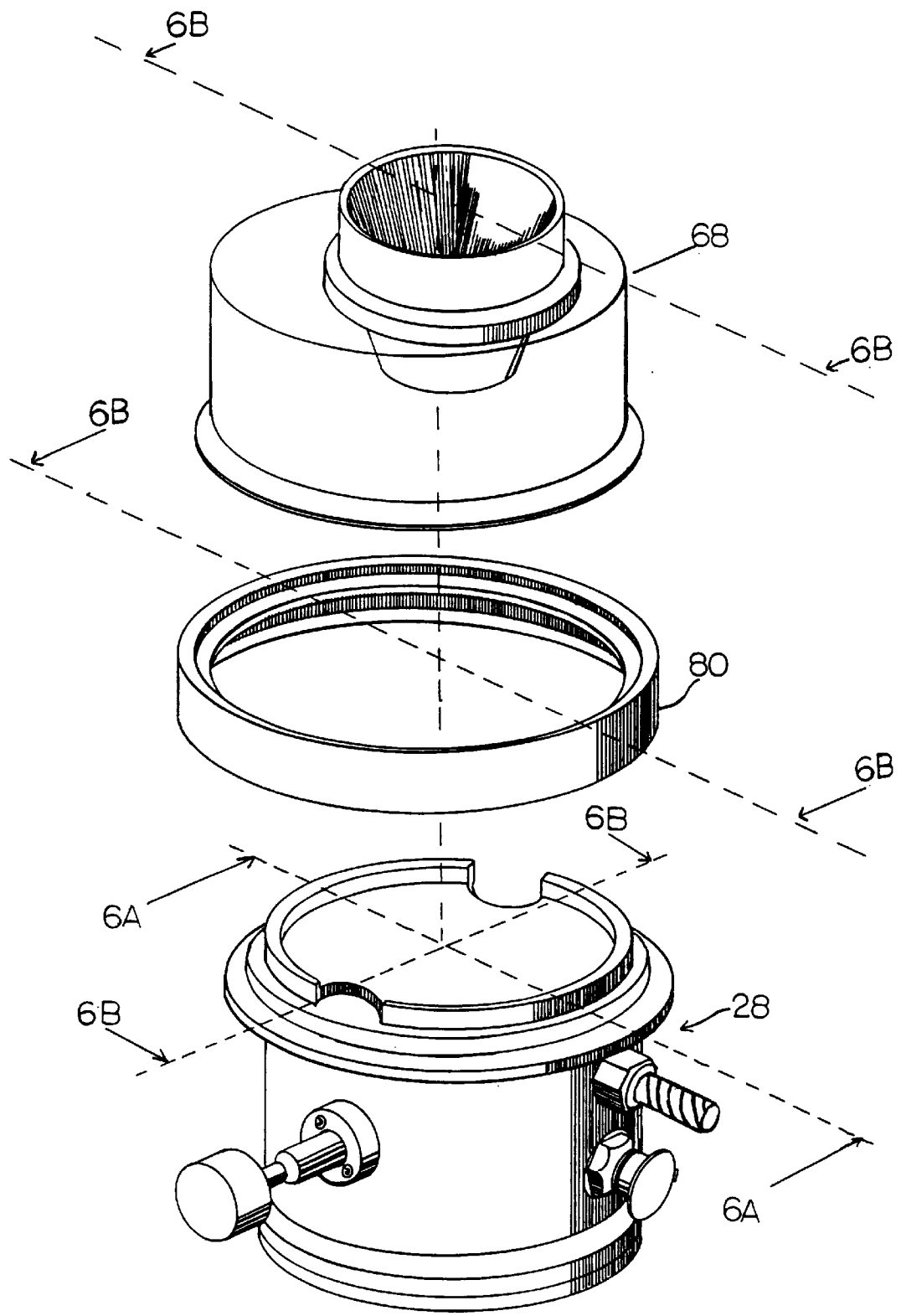
FIG. 2 is a perspective view of the two functional assemblies of the remote sampler and the seal that connects them.
Figure 6A:
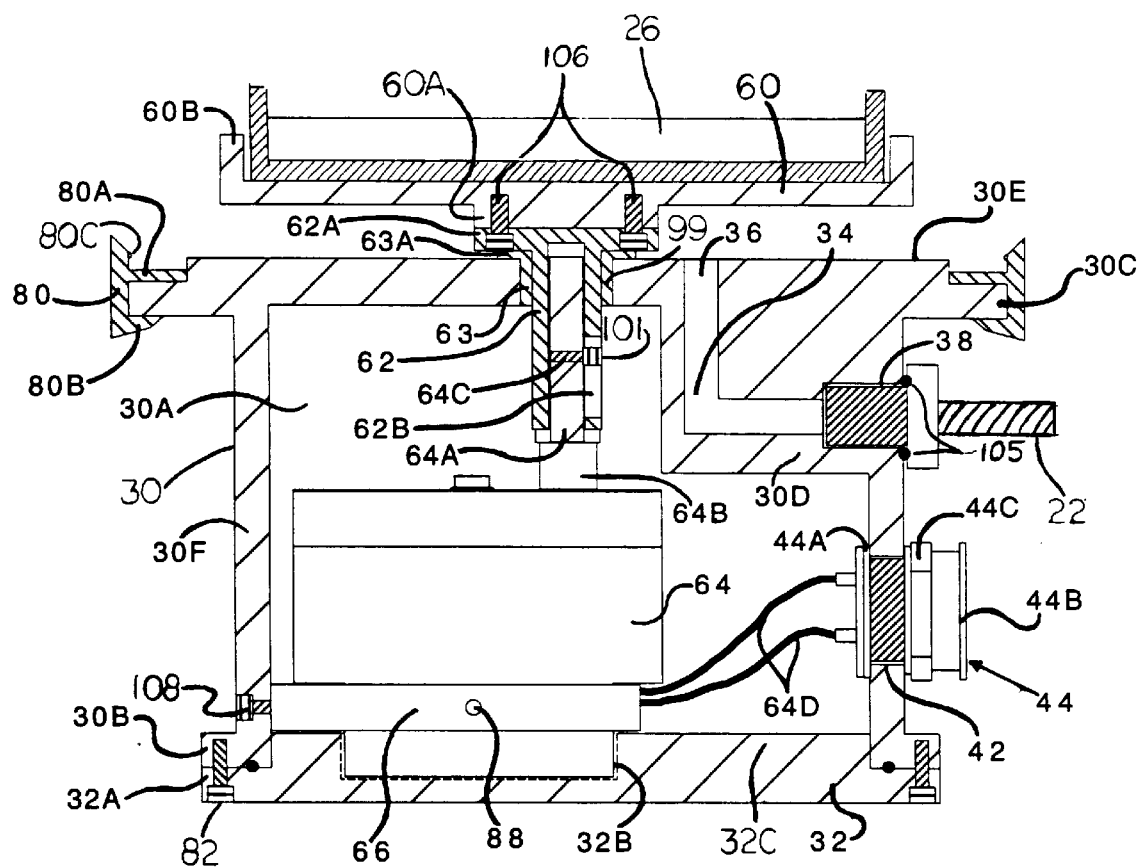
FIG. 6A is a sectional view through the base assembly of the remote sampler showing its components.
Figure 6B:
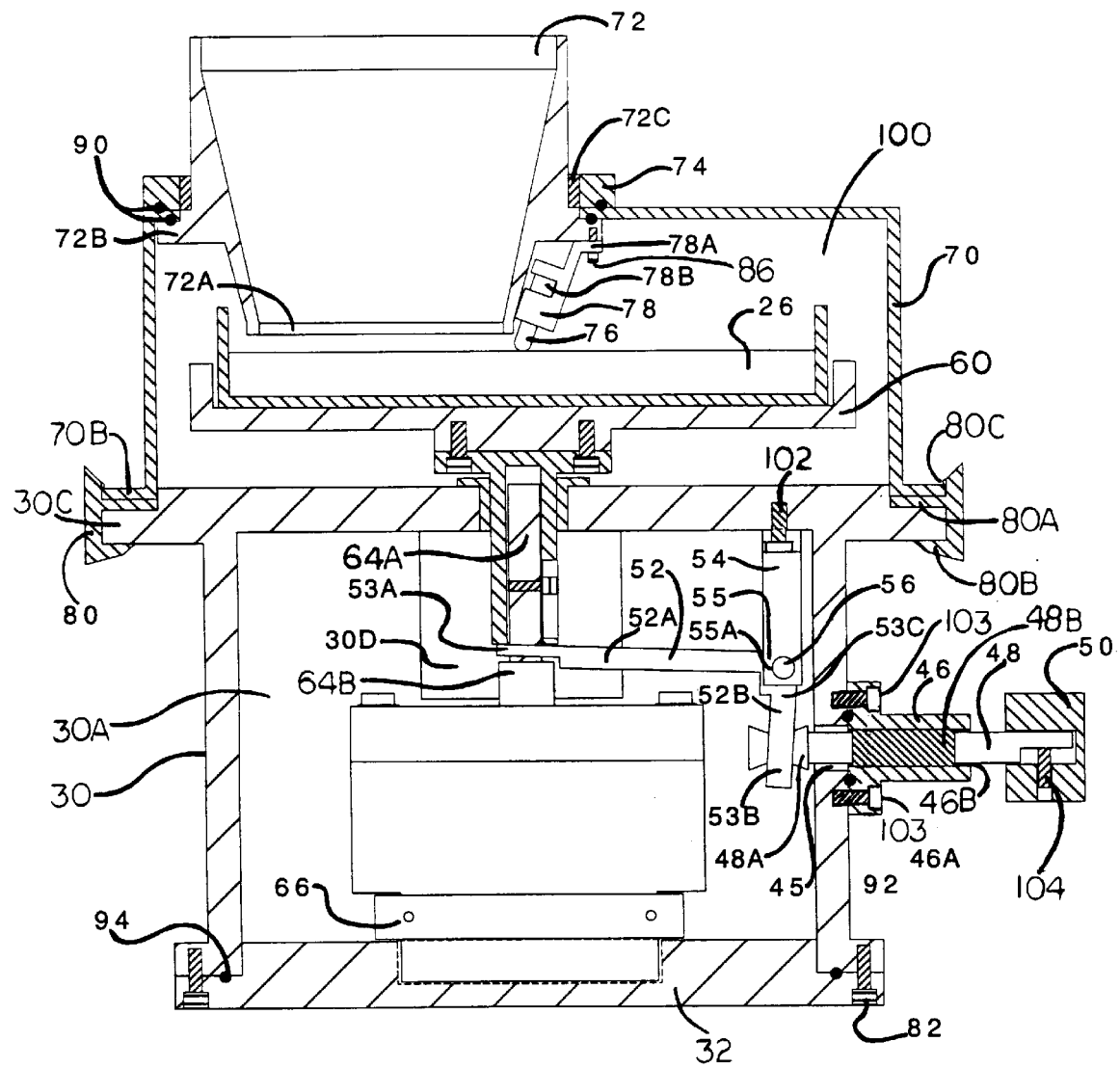
FIG. 6B is a sectional view of the base and dome assemblies of the remote sampler showing their components.

As depicted in FIG. 2, the remote sampler is comprised of two main functional assemblies, a base assembly 28, and a dome assembly 68. Sandwiched between these two assemblies is a dome-to-base seal 80. Dome-to-base seal 80 seals dome assembly 68 to base assembly 28 forming a sealed sample chamber 100, at the exterior top surface of a base 30, best depicted in FIGS. 1 and 6B. As best depicted in FIG. 6B, within the sealed sample chamber is a turntable 60 mounted on a turntable shaft 62 which rotates within a turntable bushing 63 located in a circular aperture 99 in the top center surface of the base. The turntable shaft is adjustably attached to a turntable drive mechanism, a motor shaft 64A of a motor 64 located within a hollow interior 30A of the base. The turntable shaft, attached turntable and a test plate 26, located on the turntable, are slowly rotated during operation when operative rotational power is supplied from the motor.

Referring to FIG. 6B, a sample conduit 72 with a slit-type sample inlet or sample slit 72A cut transversely through its floor, projects through the top surface of the dome, into the sample chamber, locating it approximately midway between the center and periphery of the turntable and the test plate. As depicted in FIG. 7B, the test plate is vertically adjusted to a predetermined distance beneath the slit with a turntable adjustment means 98 in conjunction with a distance indicator 76 and a indicator mount 78. When vacuum is supplied to a vacuum receptacle 40 of the base, from the controller means during operation, a constant flow of air enters through the sample conduit and sample slit impacting particles on the surface of the test plate. As best depicted in FIG. 6A, the sample air volume is evacuated from the sample chamber through a air outlet 36 at the top surface of the base. The sampled air volume is then drawn through airway 34, out of vacuum receptacle 40. Following testing, incubation of the test plate permits colonies to be counted, speciated and evaluated. As the volume of air sampled per specified time period is known, the density of bacterial organisms per volume of air can then be determined. Moreover, as the rotational speed of the turntable is known the time of organismal capture may also be determined.

Figure 3:
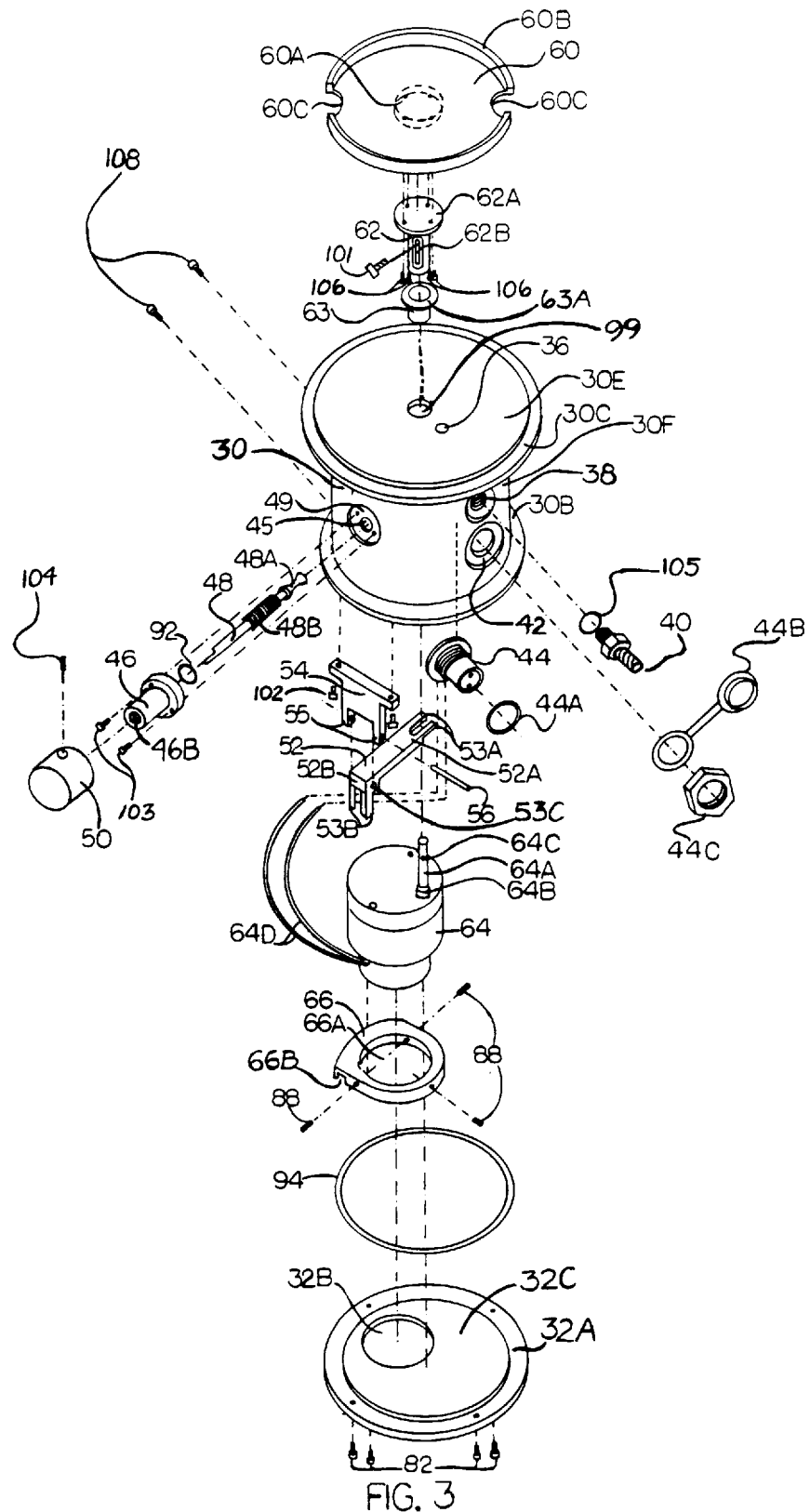
FIG. 3 is an exploded perspective view of the base assembly of the remote sampler.

As depicted in FIG. 3 (exploded view) and FIG. 6B (sectional view), is the main support structure of base assembly 28, a base 30. Base 30 is cylindrical in shape with a laterally extending upper flange 30C which encircles the circumference of the top surface of the base. The outer perimeter of upper flange 30C is of a predetermined thickness which fits with close tolerance between a seal flange 80A and a bottom lip 80B of dome-to-base seal 80, as depicted in section in FIG. 6B. As depicted in section in both FIGS. 6A and 6B, the hollow interior of base 30 is cylindrical in shape, being closed at its top, but open to the bottom of the base. The interior of the base houses the turntable elevation and rotational means. The material thickness between the interior and exterior surfaces of the base, comprising a trunk 30F, allows for mounting of these components. A laterally extending lower flange 30B, which is as wide as it is thick, encircles the perimeter of the bottom edge of the base. Lower flange 30B of base 30 allows attachment of a base cover 32 and may also be utilized for removably affixing the remote sampler to other surfaces.

As depicted in FIGS. 3 and 6B, base cover 32 is circular in shape having a center cylindrical extension 32C which fits with very close tolerance into the bottom portion of the interior of base 30. A motor relief 32B in the cylindrical extension, located between its peripheral edge and approximate center, accepts the lower portion of a motor 64. A laterally extending base flange 32A, with a width which is substantially equivalent to the combined width of the trunk and lower flange 30B of the base, encircles the cylindrical extension. The base cover is attached to the base with a plurality of base cover screws 82, or otherwise, but should be easily removable and replaceable.

Both the base and the base cover of the sampler are manufactured from aircraft grade, 6061-T6 Aluminum. Aluminum was employed in the current embodiment for its light weight, as the unit is portable and may be moved from location to location and additionally for its substantial resistance to chemical sanitization procedures. The surface finish of these components are essentially non-porous and non-particulate generating. The non-porous finish employed disallows entrapment of particulate matter and allows complete cleaning and sanitization of the surface which may be performed using a variety of disinfectant agents such as quaternary disinfectants, alcohol, bleach, hydrogen peroxide, or other commonly used disinfecting agents. The surfaces of these components have also been clear anodized to help protect the materials and to give the device an appealing clean looking appearance.

Additional embodiments of the base and base cover may include construction from a variety of materials including alternate grades of aluminum such as 2024-T4, corrosion resistant stainless steels, titanium, bi-metals, plastics, or other materials that would offer the same structural functionality. The base and base cover may be formed by a variety of methods such as molding, casting, or machining, or may be formed from a combination of molding or casting and machining or otherwise. Surface finishes of aluminum may include standard anodizing (i.e., clear, blue, red, gray, or black finish), hard anodizing, or chromic anodizing. Painted finishes may be employed, but would have to be of durable, high quality non-shedding, non-toxic paints, able to withstand sanitization methods described. Preferably, the materials and surface finish must not generate or harbor particulate matter which could contaminate the environment in which the remote sampler is to be utilized and must be resistant to repeated sanitization procedures described previously.

As depicted in section in FIG. 6A, a portion of the base interior materials have not been excavated. This portion of the interior, a block 30D, houses a airway 34. Airway 34 travels horizontally through the trunk of the base from the exterior side from a vacuum port 38, into block 30D. Airway 34 then travels vertically through block 30D opening at a air outlet 36 at the top surface of the base. As depicted in FIGS. 3 and 6A, at vacuum port 38, airway 34 is threaded to accept vacuum connector 22. A vacuum O-Ring 105 sandwiched between the vacuum connector and the exterior side of the base creates a substantially air tight seal when the vacuum connector is threaded into airway 34 at vacuum port 38. The vacuum receptacle allows attachment of a vacuum means to the airway, to allow air to be drawn into the sample chamber through the sample conduit and sample slit, and then be evacuated from the sample chamber, through the air outlet. Additional embodiments may employ other means, such as utilizing a variety of tubing and vacuum fitting combinations, to create an airway which would allow air to be drawn into and then evacuated from the sample chamber, preferably below the level of the test plate to assure the sample volume contacts the test plate surface.

As depicted in FIGS. 3 and 6A, below vacuum port 38 of base 30 is electrical port 42. Electrical port 42 is an opening in the exterior side of base 30 through the trunk into the interior, which accommodates electronic receptacle 44. Electronic receptacle 44 transfers power from the controller means by way of a power cable 14 depicted in FIG. 1, to the motor housed within the interior of the base. Motor 64 is operatively wired to the electronic receptacle by solder or other means. In the current embodiment, electronic receptacle 44 is a Conxall® type 7282-3PG-300, connector, available from numerous electronics suppliers. The electronic receptacle 44, with a gasket 44A (a component of electronic receptacle 44) is mounted within the trunk of the base from its interior. A weather seal 44B is a Conxall® type 6295, weathertight cap. The weather seal is placed over the end of electronic connector 44 which extends through electronic port 42. The threads of a locking ring 44C (a component of electronic receptacle 44) are engaged with the threads of electronic receptacle 44 which extend through the trunk of base 30. Locking ring 44C is adequately tightened to secure electronic receptacle 44, gasket 44A, and weather seal 44B to the base. The electronic receptacle described is for illustrative purposes as it is compact and has substantial air and water tight sealing capabilities which minimize the chance of electrical hazard. A variety of electrical connectors may be used in additional embodiments which would offer the same preferred characteristics.

Turntable 60, depicted in FIGS. 3 and 6A, is circular in shape with an upstanding peripheral lip 60B which encircles its top surface. The lip is roughly half the height of test plate 26 and the circular area contained within the lip is large enough to accept the test plate. Test plate 26 is a standard 100 mm agar plate routinely employed throughout laboratories and readily available from numerous commercial suppliers. Currently, such an agar plate consists of a standard circular petri dish having an upstanding peripheral lip partially filled with a layer of agar growth medium or equivalent, as is very well known. A variety of medias are available for air quality monitoring. The media of choice is dependent on the organisms one wishes to recover, as well as the environment in which testing is to be performed. A pair of turntable finger relief's 60C, depicted in FIG. 3, have been cut into the periphery of the turntable 60 and lip 60B, roughly 180° degrees from each other, to allow easier placement and extraction of the test plate by the operator.

Referring to FIGS. 3 and 6A, at the bottom surface of the turntable is a short cylindrical extension 60A which is substantially equivalent to the circumference of a shaft flange 62A of turntable shaft 62. Shaft flange 62A, extends laterally from the top surface of turntable shaft 62 encircling its circumference. The shaft flange allows attachment of turntable shaft 62 to the cylindrical extension of the turntable with a plurality of flange screws 106 or otherwise. The circumference of the turntable shaft, inferior to the flange, fits within turntable bushing 63 which is located within circular aperture 99 in the top center surface of the base. Very close tolerances are kept between turntable bushing 63 and turntable shaft 62 to aid in sealing the interior of the base from the environment. The bushing allows smooth rotation of the turntable shaft as it is formed of bronze, although other low friction materials may be employed. Additionally, a bushing flange 63A, extending laterally from the top circumference of the bushing, resides atop the base, disallowing the turntable flange to cause wear to the top surface of the base when the turntable is rotated at its lowest setting.

The center hollow cylindrical interior of turntable shaft 62 opens downwardly to accept motor shaft 64A. A slot 62B, opens through the side of the shaft into the hollow interior. The head of a turntable shaft screw 101, engaged with the threading of a shaft hole 64C of motor shaft 64A, resides within the slot. By this arrangement the turntable shaft is movably attached to the motor shaft, allowing, but limiting, vertical movement of the turntable shaft about the length of the motor shaft. Thereby, limiting the minimum and maximum height adjustment of the turntable shaft and affixed turntable 60.

The turntable shaft in the current embodiment has been machined out of 316 stainless steel. Although, other comparable materials may be employed including other grades of stainless steel, aluminum, titanium, or plastics, which would allow the same functionality and be able to withstand disinfection procedures with a variety of chemical sanitants. The turntable is fabricated out of 6061-T6 aluminum for its light weight and resistance to the aforementioned disinfection procedures. Although, although other materials may be utilized such as stainless steel. Additional embodiments may include such modifications as one piece construction of the turntable shaft and turntable, or may employ a test plate support structure consisting of a plurality of arms projecting out in a radial fashion from the turn table shaft with which to hold the test plate.

Depicted in FIGS. 3 and 6A, is the turntable drive mechanism employed in the current embodiment of the remote sampler which is comprised of a motor 64 in conjunction with motor shaft 64A. Motor 64 is an electric motor, although other means such as a clock type mechanism may be incorporated as the turntable drive mechanism in additional embodiments. Rotation of the turntable and thus test plate is crucial to the desired function of the remote sampler as further described. Firstly, the rotation removes bacterial organisms from the direct path of incoming air from the sample slit after they have been impinged or captured on the test plate. This keeps the bacterial organisms from desiccating and thus allows for a lengthy sample period. Secondly, the rotation evenly distributes the bacterial organisms over the test plate surface. This even distribution allows for easier enumeration of bacterial organisms recovered as they are not impinged or captured on top of one another. Thirdly, the rotation permits determination of the time of recovery of bacterial organisms captured as the rotational distance of the test plate is equivalent to a known time period. Determination of the recovery time then allows for correlation of recovered contaminants with specific operations under way in the controlled environment.

In the current embodiment of the remote sampler the turntable drive mechanism rotates the turntable and thus test plate at speed of 1 revolution per hour. However, a variety of rotational speeds may be employed if appropriately validated for organismal recovery. For example rotational speeds faster than 1 revolution per hour would be acceptable and may be required depending on the quality of the air to be monitored. An environment with a high density of airborne baterica, may require a higher rotational speed of the test plate. When the test plate is rotated faster the bacterial organisms captured are spread out more evenly over the entire test plate surface as opposed to being captured on top of one another allowing more accurate enumeration of the organism recovered in a highly contaminated area. Additional embodiments may include rotational speeds such as one revolution in 5, 10, 15, 30 or 120 minutes. Different speeds may be obtained by means such as varying gearing of the turntable drive mechanism or by altering the cycles of electricity to the turntable drive mechanism if an electric motor is employed. If motor speeds faster the 1 revolution per hour are employed, it is preferred that the test plate be exposed for sampling for no more than one full rotation as the same portion of the test plate should not pass the sample slit more than once for reasons including: over exposure and desiccation of bacterial organisms which were captured on the test plate during the first exposure, capture of organisms upon one another making enumeration difficult and inability to estimate the recovery time of bacterial organisms captured as it would not be known at which rotation the organisms were recovered.

Referring to FIGS. 3 and 6A, in the current embodiment of the device the turntable drive mechanism is attached to the interior of the housing by a motor mount 66. A hole 66A through the center of the mount accepts the base portion of motor 64. The motor mount 66 is attached to the interior side of the base with a pair of motor mount screws 108 which are employed from the exterior side of the base, through the trunk, roughly 180° from vacuum port 38. The motor is affixed in place in the motor mount with a plurality of set screws 88, but other suitable means of attachment are of course possible. A relief 66B at the bottom back of the mount, adjacent to hole 66A, allows clearance for an motor wires 64D. Additional embodiments may include modifications to the mounts design in order to retain the motor within the interior or in which to incorporate the use of other motors in additional embodiment. In the current embodiment of the remote sampler, motor mount 66 is manufactured from 6061-T6 aluminum but other materials such plastics or stainless steel may be employed.

FIGS. 3 and 6A depict the turntable adjustment means employed in the current embodiment of the remote sampler, to adjust the operating height of a turntable 60 in relationship to the exterior bottom surface of the sample conduit and the sample slit. The turntable adjustment means includes the following components: a lever arm 52, a lever mount 54, a retaining pin 56, a shaft hangar 46, a shaft 48, and a adjustment knob 50.

As best depicted in FIG. 6B, lever arm 52 is "L" shaped. At the distal end of a long access 52A of lever arm 52 are a pair of tines 53A. Tines 53A reside at the base of the turntable shaft and around motor shaft 64A, residing atop a motor bushing 64B when at its lowest position. A short access 52B of lever arm 52 is roughly half the length of the long access 52A. A beveled tines 53B project from the end of the short access. The inside edges of the tines are beveled at roughly a 45° angle. Beveled tines 53B fit with close tolerance over the center of a working end 48A of a shaft 48.

The lever arm operates in conjunction with a lever mount 54. Lever mount 54 is "T" shaped and acts as the fulcrum for lever arm 52. Extending from the lower portion of the "T" are posts 55. The area between posts 55 accept a pivot point 53C of the lever arm. A mounting hole 55A perpendicular to and continuous through the sides of posts 55, near their distal ends, and through pivot point 53C, accepts a retaining pin 56 which pivotably attaches lever arm 52 to lever mount 54. The lever mount and attached lever arm is located at the interior top surface edge of the base, 90° from vacuum port 38, with the longer access of the lever arm oriented parallel to interior top surface of the base and the shorter access oriented perpendicular to the top surface and parallel to the interior side, of the base. A pair of lever mount screws 102 passing through the laterally extending appendages of the "T", secure the lever mount in this location, but may be otherwise secured.

Shaft 48 and shaft hangar 46, depicted in FIGS. 3 and 6B, work in conjunction with the lever arm and the lever mount acting as the means for applying force to the lever arm within the interior of the base. Shaft hangar 46 is cylindrical in shape with a hollow threaded center. A laterally extending hangar flange 4 6 encircles the circumference of the shaft hangar at one end for attachment of the shaft hangar. The hangar flange is attached to the exterior side of the base, at attachment point 49, with a pair of hangar flange screws 103. The screws do not penetrate into the interior of base 30 as to minimize entry holes into the interior which would require sealing. Other means may be employed to attach the shaft hangar to the exterior side of the base in additional embodiments. For example, the shaft hangar may be threaded into the base to minimize attachment hardware and relieve the need for hangar flange 46A.

As depicted in FIGS. 3 and 6B, shaft 48 is threaded around roughly ⅓ of its length to allow engagement with a hangar threading 46B of the interior of shaft hangar 46. A shaft threading 48B is engaged with the hangar threading from the interior of the base through a clearance hole 45. Clearance hole 45 is wide enough in diameter to accept the threaded portion of the shaft but not so wide as to accept a working end 48A of the shaft so as to retain in within the interior of the base. Working end 48A of shaft 48, shaped as two cones attached end to end at their smaller diameters, resides between the beveled tines of lever arm 52 within the interior of the base. The angular surfaces of the working end of the shaft, in conjunction with the angular surfaces of the beveled tines of the short access of the lever arm, allow pivotability of the short access of the lever arm over the working end of the shaft. This functionality permits the application of force to the short access of the lever arm from either side of the lever arm. When the shaft is threaded into the shaft hangar from the exterior the short access of the lever arm travels forward, raising the long access of the lever arm and thus the turntable shaft and attached turntable. When the shaft is threaded out of the shaft hangar the short access of the lever arm travels rearward, lowering the long access of the lever arm and thus the turntable shaft and turntable. Additionally, a adjustment knob 50 is attached to the other end of shaft 48 for ease in gripping and rotating the shaft. Knob 50 has a hollow center which accepts the end of shaft 48 and is attached to the shaft with a knob set screw 104 or by other means.

In the current embodiment of the sampler of the present invention the turntable adjustment lever means, lever arm 52, lever mount 54, retaining pin 56, shaft 48, shaft hangar 46, and knob 50, are machined out of 316 stainless steel. However, other embodiments of the device may employ a variety of materials from which to fabricate these components. The materials of choice should be resistant to wear and corrosion from chemical sanitants such as alcohol, quaternary disinfectants, hydrogen peroxide, and bleach. Comparable materials may include other grades of stainless steel or aluminum and should be substantially non-porous and non-shedding but should be durable so as to perform the required functionality routinely with negligible wear. Additional embodiments may employ a variety of lever or other means, which are well known, to achieve the vertical height adjustment of the turntable.

As an object of the remote sampler is to assure that the device does not contaminate the controlled environments in which it is utilized, the interior of the base is sealed in an substantially air tight manner from the exterior environment to prevent contaminant ingress and egress. As such, entrance holes into the interior of the base from the exterior, which are utilized for mounting of components described heretofore, are substantially sealed. In the current embodiment of the remote sampler this objective is obtained by the means described forthwith.

As depicted in FIG. 6B, a base cover O-Ring 94 is sandwiched between the mating surfaces of base cover 32 and the base, sealing the largest opening into the base interior in a substantially air and water tight manner. In a like manner, a shaft hangar O-Ring 92 is sandwiched between shaft hangar 46 and the exterior side of the base at attachment point 49 when the shaft hangar is attached by a pair of flange screws 103. Additionally, the fine threading of shaft 48 and shaft hangar 46, in conjunction with a lubricant, forms a substantial seal along the engaged threading of these two components, sealing clearance hole 45. Furthermore, as depicted in FIG. 6A, the weathertight connector and gasket 44C, of electrical connector 44, assure a substantially air and water tight seal with the exterior and interior surfaces of base 30 substantially sealing the electrical port. Moreover, Teflon® tape is employed on the threads of motor mount screws 108, of motor mount 66, to form a substantial seal when engaged with threading in the base. Further, the tight tolerances between turntable bushing 63 and turntable shaft 62, in conjunction with a lubricant, substantially reduce any chance of contaminant egress or ingress at this opening as well. Lastly, the turntable bushing is pressed to fit into the circular aperture in the top surface of the base with extremely tight tolerances leaving no entrance points into the interior between these surfaces.

With this arrangement contaminates may not enter or leave the base interior and as such can not influence the samples gathered with the device and may not add to the bioburden load of the controlled environment, products, or test materials which may be manipulated therein. Additionally, this seal arrangement allows the remote sampler to be easily and completely cleaned and sanitized as all surfaces left exposed to the environment are sanitable with chemical disinfectants. Of course, additional embodiments may employ a variety of means for sealing entrance holes made into the interior for attaching components to the base. This may include the employment of gaskets, sealants, or other means, in place of, or in conjunction with 0-Rings for sealing entrance holes into the base interior disallowing contaminants ingress and egress. Although, it is preferred that other means employed allow ease of assembly and disassembly of components.

Figure 4:
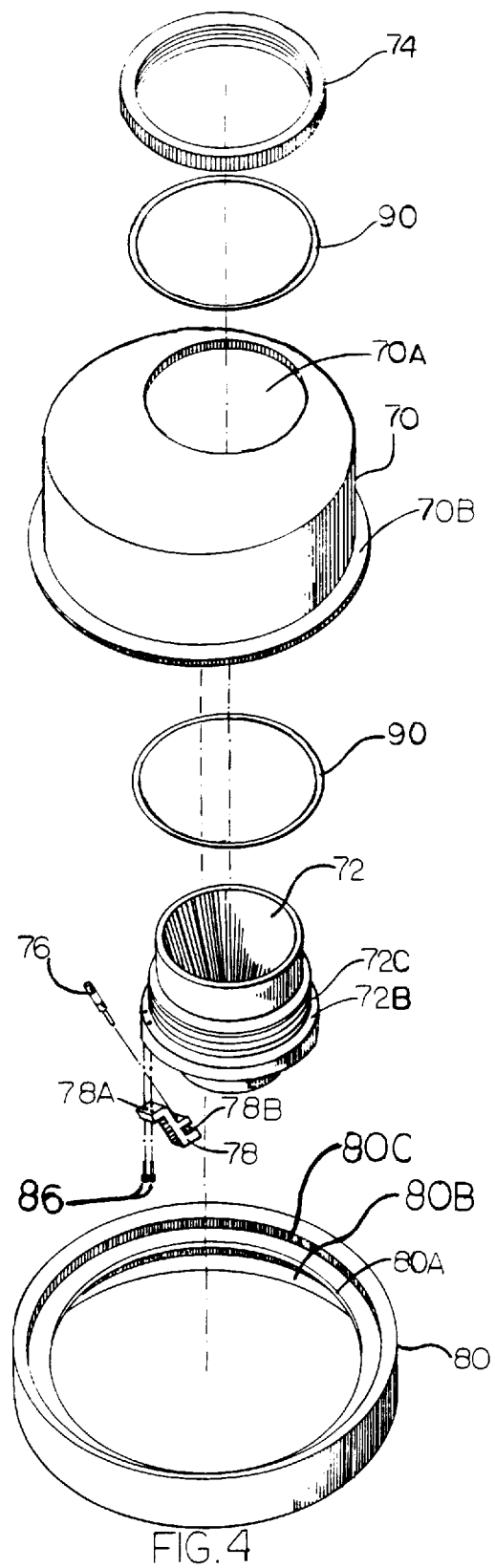
FIG. 4 is an exploded perspective view of the dome assembly and seal of the remote sampler.
Figure 5:
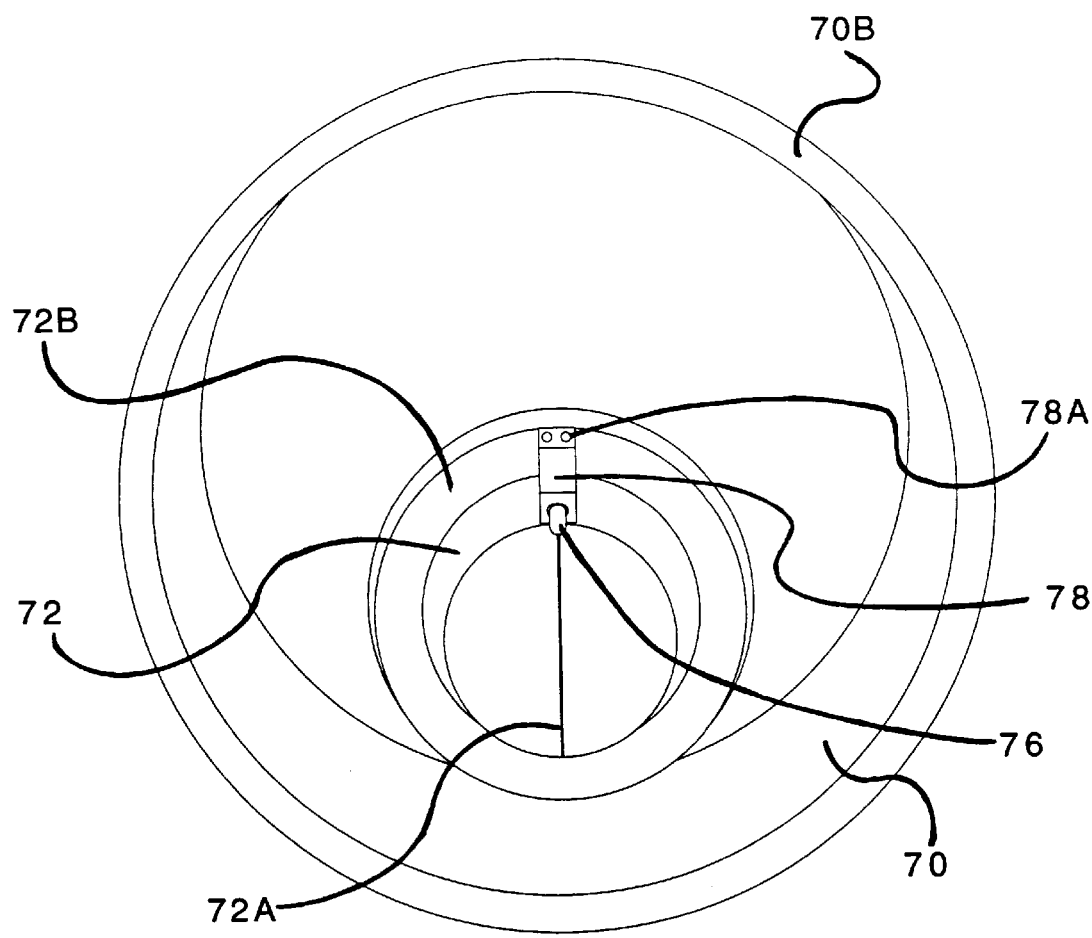
FIG. 5 is a perspective view of the dome assembly from the interior.

FIG. 4 shows an exploded perspective view of the dome assembly 68. The dome assembly 68 consist of a dome 70, sample conduit 72 with sample slit 72A (best depicted in FIG. 5), a O-Ring (035) 90, a mounting ring 74, distance indicator 76, and a indicator mount 78. These components are described in detail in the following text as utilized in the current embodiment of the remote sampler of the present invention.

Referring to FIGS. 4 and 6B, dome 70 is of sufficient size to contain the turntable and the test plate on the top surface of the base. The bottom of dome 70 is open with a laterally extending flange 70B which encircles its circumference at its bottom edge which is substantially equivalent to the outer diameter of the upper flange of the base. Dome flange 70B allows removable attachment of dome 70 to the base in conjunction with dome-to-base seal 80 whereby forming sealed sample chamber 100. As best depicted in FIG. 6B, sealed sample chamber 100 is in itself a controlled environment. Sealed sample chamber 100 allows impaction of the sampled air volume and associated contaminants on the test plate, while disallowing incidental contaminants from being deposited thereupon, whereby the density of bacterial contaminants in a specified volume of air can be accurately determined. The top of the dome is solid and planer with a dome hole 70A having a circumference which accepts a conduit threading 72C of sample conduit 72. Hole 70A is located such that it orients the sample conduit between the center and exterior edge of turntable 60.

In this embodiment dome 70 is thermo-molded of clear Polycarbonate, as to allowing viewing of components that reside within the interior of the sealed sample chamber as depicted in FIG. 6B, as is desired for set up and operation. Polycarbonate is used to form the dome as it is considerably resilient to deterioration from chemical disinfectants such as alcohol, quaternary disinfectants, and to steam sterilization procedures. Additionally, polycarbonate may be durable as to withstand impacts from heights of roughly 1–2 meters as might occur during manipulations or transport of the remote sampler. Polycarbonate is also substantially non-porous as not to entrap contaminants and is essentially a non-particulate generating material. However, the dome may be constructed of other materials which may offer these preferred characteristics and/or may be created by others methods such as injection molding, or machining and polishing of block materials such as polycarbonate. The dome may also be configured differently such as being of stainless steel or aluminum with single or multiple ports for viewing the interior components.

The construction of the sample conduit is depicted in detail in FIGS. 4 and 6B. The exterior diameter of the sample conduit which extends from the exterior top of the dome is cylindrical in shape. A laterally extending conduit flange 72B encircles the exterior portion of sample conduit 72 at the base of the cylindrical portion of the conduit and resides against the interior top surface of the dome, surrounding dome hole 70A. As best depicted in FIG. 6B, below conduit flange 72B the exterior of the sample conduit is conical in shape having non-parallel sides tapering inwardly towards its circular bottom surface which is of a size that permits the lower portion of the sample conduit to reside between the center and peripheral edge of the test plate. Above conduit flange 72B is conduit threading 72C which fits with close tolerance within dome hole 70A. Conduit threading 72C allows attachment of mounting ring 74 described directly.

Mounting ring 74 is depicted in detail in FIGS. 4 and 6B. The interior circumference of mounting ring 74 fits closely over the cylindrical top of the conduit and is threaded to engage with conduit threading 72C which secures the conduit flange and mounting ring tightly against the interior and exterior top surfaces of the dome. O-Rings (035) 90, sandwiched between the conduit flange and the interior top surface of the dome, and also between the mounting ring and the top surface of the dome, seal the sample conduit to the dome in a substantially air tight manner. Additionally, the top surface of the mounting ring conceals the threaded portion of the sample conduit minimizing contamination that may be harbored by the threads. With this arrangement, mounting ring 74 removably attaches and substantially seals the sample conduit 72 to dome 70 in conjunction with conduit flange 72B and O-Rings (035) 90.

Referring to FIG. 6B, the interior of sample conduit 72 is funnel shaped with an initial opening circumference which is slightly smaller than the outer circumference of the upper conduit, tapering to a bottom circumference which is slightly smaller than the outer circumference of the conically shaped exterior bottom. The interior shallow bottom floor of the conduit is solid and planer with narrow sample slit 72A (depicted in FIG. 5) of a predetermined width cut transversely across and through its diameter. The length and width of the sample slit, in combination with the volume of airflow that passes through the sample slit in a specified time period, determine the velocity to which air and air borne bacteria may be accelerated and impacted on the test plate. A variety of slit widths may be employed depending on the characteristics of the organisms one is attempting to recover and/or the volume of air one wishes to sample in a predetermined time period. It is crucial though that the impact velocity is sufficient as to assure capture of the organisms on the test plate, but not so great that the organisms are damaged and thus made non-viable. For example, studies have shown that impact velocities ranging from 40 to 130 meters per second may be employed to achieve organismal recovery, but others may also be validated and employed.

Additionally, the distance between the sample slit in the bottom of the conduit and the test plate is also crucial. The greater the distance between the test plate and sample slit the lower the impact velocity of the sample air volume and associated bacterial organisms will be with the test plate. If the distance is to close, the organisms may be damaged and become non-viable. If the distance is to great, organisms may not be maintained on the test plate surface and may remain within the sampled air volume which is evacuated from the sample chamber. Therefore, it is preferred that a predetermined distance need be set between the sample slit and test plate surface. In the current embodiment of the resent invention this predetermined distance is measured with distance indicator 76 and indicator mount 78 discussed forthwith.

Referring to FIGS. 4 and 6B, a distance indicator 76 is included to permit the operator to determine the proper height of the sample slit above the test plate surface. The distance indicator 76 is cylindrical in shape. A lower portion of distance indicator 76 is narrower than the upper portion of the indicator and fits through the opening on the bottom of indicator mount 78. The upper section of the indicator is wider in diameter than the opening in the bottom of indicator mount 78 keeping it from dropping out. The bottom of the indicator is rounded as it is intended to ride upon the surface of the test plate. The surface of the upper portion of indicator 76 is red anodized with a non-anodized central portion which corresponds in size to a side relief 78B of indicator mount 78, which is substantially equivalent to the predetermined distance between the test plate and bottom of the sample slit.

Indicator mount 78 is attached by a mounting flange 78A to the bottom surface of conduit flange with a pair of screws 86 in alignment with the end of the sample slit which is oriented near the center of the dome. The mounting flange extends from the top of the indicator mount at an angle which orients the indicator mount in a parallel alignment to the exterior side of the conically shaped lower portion of the sample conduit. This mounting location places the rounded bottom of the distance indicator at the approximate center of the test plate during operation. As depicted in FIG. 7B, when the indicator is at the appropriate height in indicator mount 78, the red anodized portions of the indicator are not visible. As depicted in FIG. 7A, when the indicator is to low, the top anodized portion of the indicator is visible through side relief 78B. As depicted in FIG. 7C, when indicator 76 is to high, in indicator mount 78, the red anodized portions of indicator 76 are visible at side relief 78B and on top of indicator mount 78. With this arrangement, distance indicator 76 indicates proper or improper height adjustment of test plate 26 and turntable 60 in relationship to sample slit 72A.

Sample conduit 72, mounting ring 74, distance indicator 76, and indicator mount 78 have all been machined from aircraft grade, 6061-T6, aluminum. Other comparable materials may be used to create these components such as other grades of aluminum, stainless steel, titanium, or plastics. However, the materials must employ a non-porous surface finish, be substantially non-particulate generating, be able to withstand repeated disinfectant procedures by chemical sanitants or steam sterilization procedures with negligible degradation.

Depicted in FIGS. 4 and 6B, dome-to-base seal 80 removably attaches and seals the dome assembly to the base assembly, in a substantially air tight manner, forming sealed sample chamber 100, described heretofore. Seal 80 is ring shaped with an interior circumference which is substantially equivalent to the outer circumference of upper flange 30C of the base and dome flange 70B. A seal flange 80A encircles the center circumference of seal 80 at a 90° angle to the interior side. Seal flange 80A is as wide as the outer perimeter of upper flange 30C of the base and is the main sealing surface of seal 80 between the dome assembly and base assembly. A bottom lip 80B encircles the inner diameter at the bottom edge of the seal and is roughly ⅔ the width of seal flange 80A. The gap between the seal flange and bottom lip is essentially equivalent to the thickness of the outer perimeter of the upper flange and seats around the upper flange with close tolerance sealing it tightly in place. This alleviates the requirement for adhesives to mount the seal to the base, allowing the seal to be routinely removed and replaced for sanitization or other purposes. As depicted in FIG. 6B, a small extension 80C, shaped as a half circle, encircles the interior circumference at the top edge of the seal. This extension securely but removably affixes the dome flange within the circumference of the seal, holding it tightly against the seal flange when the dome assembly is seated in the seal, forming a substantially air tight seal between these components.

Seal 80 is molded out of polyethylene and is fairly pliable as to form a substantial seal between components, yet elastic enough to retain its original shape which fits tightly on upper flange 30C and dome flange 70B. A variety of materials may be used to make seal 80 such as Viton®, butyl, silicones or other materials. However, it is preferred that the materials have the qualities of being low particulate shedding and be able to withstand repeated disinfectant procedures by a variety of chemical disinfectants and steam sterilization procedures. Instead of incorporating attachment mechanisms into the seal as in the current embodiment, other seal means may be employed. For example, a flat, circular gasket, or O-Ring sandwiched between the dome and base, with clamping mechanisms employed to hold the dome and base tightly against it may be employed.

For, operation, the remote sampler is operatively connected to controller means for operation of the turntable drive mechanism and the vacuum means employed to supply air flow through the sealed sample chamber. As depicted for illustrative purposes in FIG. 1, controller means 8 is the means employed for operative control of the turntable drive mechanism and vacuum means in the current embodiment of the remote sampler. The controller means is connected to an in house power supply and is functionally wired to operate supply power to a vacuum pump (not shown) housed within the controller means which is employed as the vacuum means, and to the turntable drive means, motor 64 in conjunction with motor shaft 64A, in the remote sampler.

As depicted in FIG. 1, operative power is transferred from the controller means to the turntable drive mechanism in the remote sampler through power cable 14. At one end of power cable 14 is soldered a socket connector 16, a Conxall® Type no. 6282-3SG-3XX connector, which mates with an electronic receptacle 44, a Conxall® Type no. 7282-3SG-300 connector, mounted on the remote sampler as described heretofore. On the other end of the power cable is soldered a pair of banana plugs 18, which connects to the banana jacks 27 on the exterior of the controller means (Electronic connectors described are available from numerous electronics distributors). The connectors described are for illustrative purpose as they employ characteristics that are preferred in the current embodiment of the remote sampler. Other comparable wiring, connectors and fittings which would transfer power from controller means 8 to the remote sampler 10 may be utilized in additional embodiments. However, it is preferred that other power cable assemblies allow for quick connect and disconnect capabilities, be compact in size and offer scaling means which substantially minimize electrical hazard.

Vacuum line 20 transfers air flow from the vacuum means housed in the controller means to the remote sampler. One end of vacuum line 20 is removably attached to a vacuum connector 22 threaded into vacuum receptacle 38 of remote sampler 10 and the other end to a vacuum connector 24 mounted on the exterior surface of controller means 8, which is functionally plumbed to the vacuum pump. The vacuum connectors and tubing allow air flow between remote sampler 10 and sampler controller 8 and are of non-shedding materials that are resistant to chemical and steam sterilization procedures. Further, the volume of air to be sampled is controlled by an adjustable flowmeter 8C mounted on the front panel of the controller means.

Control of operative power to the turntable drive mechanism and vacuum means supplying air flow to the remote sampler, could be affected by connecting or disconnecting the primary power supply cable from the controller means to the power outlet. While this is all that is strictly necessary, it is preferred that the controller means include additional means for controlling the operation of these mechanisms. As illustrated in FIG. 1 the controller means may include a manual on/off switch 8D mounted upon its exterior and operatively connected to the house power supply. A indicator light 8E may also be employed to indicate if the house power supply to the controller means is on or off. Alternatively, or additionally, the control means may include a timer mechanism as depicted in FIG. 1. The timer will include an appropriate start/stop button and a display area which will visually display the output of the timer and which may be LCD, LED, or other display arrangements. It is preferred that the timer be operatively coupled with the on/off switch for automatic control of the turntable drive mechanism and vacuum means. For example, the timer and on/off switch may be connected such that operation of the switch will place the device in standby mode, with operative power being supplied to the turntable drive mechanism and the vacuum means only upon the operator pressing the start/stop button of the timer. The timer could then automatically count down the desired time period and automatically deactivate the turntable drive mechanism and vacuum means upon expiration of this time period. In such an arrangement, it is preferred that the timer include a set button or buttons which will allow the user to set a predetermined time period of operation for the turntable drive mechanism and vacuum means.

As stated, the aforementioned example is for illustrative purpose. Other controller means arrangements are of course possible and encompassed by the present invention. These may include a remote control set up which may allow the user to set the sample time period on the controller means and initiate sampling from the location of the remote sampler, or elsewhere, by means of either infrared, radio control, or by wires directly connected to the controller means. Further, a vacuum pump may not be employed in the controller means and as such an in house vacuum source may be utilized, although it may be operatively controlled through the controller means. Further, if the turntable is rotated by a means that does not require a electrical power source, such as a clock type mechanism, the remote sampler may be employed only with an in-house vacuum source. As such, a flowmeter to control the air flow through the sampler may be the only controller means required.

From the foregoing it will be seen that this invention is one well adapted to attain all ends and objects herein-above set forth together with other advantages which are obvious and inherent to the structure. As described heretofore, the overall streamline structure of the remote sampler causes minimal obstruction to laminar (unidirectional) airflow in controlled environments in which it is utilized, such as Class 100 to 100,000 clean rooms, or support areas, such as those found in pharmaceutical manufacturing facilities and hospitals. Further, the streamline structure allows placement of the remote sampler in locations in controlled environments which have minimal available work space, such as along pharmaceutical fill lines or within laminar airflow benches used for testing. Additionally, sealing of all entrance holes into the base interior, in a substantially air tight manner, substantially minimizes the risk of contaminant ingress and egress, whereby protecting the controlled environment from undesired contaminants. Also, the choice of materials employed for manufacture which are resilient to sanitization procedures, as well as the non-porous surface finish employed, shall surely minimize the chance of contaminating controlled environments by allowing complete, routine, sanitization of the remote sampler. Further, the utilization of 100 mm test plates as opposed to 150 mm test plates greatly reduces air quality monitoring cost. Furthermore, the physical separation of the operative controller means from the remote sampler, with means for allowing it to be operated remotely, greatly reduces the inherent risks of contamination of, and obstruction to, operations performed in controlled environments. By these means, the remote sampler is fashioned to be much more suitable for utilization in controlled environments than the prior art in slit impact samplers.

Obviously many modifications and variations of the present invention are possible in light of the above teachings. For example, dimensional changes internally and externally to the base and dome may of course be acceptable to accommodate alternate components used in additional embodiments of the invention (i.e., motors, levers, mounts, connectors, airway plumbing, etc.). As such, the overall dimensions of the remote sampler may be varied and shapes other than the cylindrical shape described in the current embodiment of the invention may be employed such as oval, spherical and square or rectangular with rounded edges. But, as described in the text, the substantially streamline shape and size of the remote sampler are crucial to the utility of the unit and should be taken into consideration.

It is, therefore, to be understood that while specific embodiments have been shown and discussed, various modifications may of course be made without departing from the scope thereof. Also, it will be understood that certain features and subcombinations are of utility and may be employed without reference to other features and subcombinations. This is contemplated by and is within the scope of the claims. As such, it is to be understood that all matter herein set forth or shown in the accompanying drawing is to be interpreted as illustrative, and not in a limiting sense.

The embodiments of the invention in which an exclusive property or privilege is claimed are defined as follows:

1. A remote slit impact air sampler for collecting viable air borne bacterial organisms comprising the combination of:
   a dome sandwiching a dome-to-base seal atop a base forming a sealed sample chamber, with an air outlet located within said sealed sample chamber;
   a turntable positioned within said sealed sample chamber and mounted upon a turntable shaft;
   a turntable drive mechanism mounted within a hollow interior of said base attached to said turntable shaft for rotating said turntable shaft and said turntable at a predetermined rotational speed;
   a sample conduit with a sample slit projecting through an opening in the top surface of said dome creating an inlet into said sample chamber, with said sample conduit and a sample slit located above said turntable, with means for the flow of air into said sample chamber through said sample slit and out of said air outlet, with further control means for controlling the rate of the air flow;
   a test plate located on said turntable within said sealed chamber onto which particles drawn through said sample conduit and said sample slit may be impinged;
   a turntable adjustment means employed for vertical adjustment of said turntable, whereby the surface of a medium residing within said test plate, located atop said turntable, can be vertically adjusted to a predetermined distance from the exterior bottom of said sample slit;
   a distance indicator employed to accurately measure said predetermined distance between the surface of said medium residing within said test plate and the exterior bottom of said sample slit;
   said base employed with sealing means with which to seal said hollow interior cavity from the surrounding environment, in a substantially air tight manner, at all entrance points made from the exterior of said base into said hollow interior for utility, whereby contaminant ingress and egress is restricted.

2. The remote slit air impact sampler of claim 1 wherein components are constructed from materials which are substantially non-particulate generating and of a substantially non-porous surface finish, whereby complete cleaning and sanitization of component surfaces exposed to the environment can be performed to remove contaminants so as not to jeopardize the environment in which it is utilized.

3. The remote slit impact air sampler of claim 1 wherein the overall structure is of a substantially streamline size and shape wherein:
   the presence of the device would have minimal disruptive effects on unidirectional or laminar airflow in environments in which it is utilized, whereby the integrity of the environments in which it is utilized will not be jeopardized by its physical presence;
   the presence of the device within an environment is not a hindrance to operations performed therein, whereby it may be utilized in a variety of environments;
   the device may be utilized in environments with minimal available work space, whereby its employment may not be limited to environments having only an abundance of available work space.

4. The remote slit impact air sampler of claim 1 wherein said dome-to-base seal attaches said dome to said base by means that assure a substantially air tight seal between said dome and said base whereby air flow into the sealed sample chamber may only occur through said sample slit, while allowing for ease in routine removal and replacement for servicing, said dome-to-base seal is composed of materials that allow for complete routine sanitization by chemical or steam sterilization procedures while offering resistance to rapid wear from these procedures, said dome-to-base seal is composed of materials that are of an elastic nature allowing the seal to maintain original structure while being malleable enough to allow a substantially air tight seal between said dome and said base.

5. A device according to claim 1 wherein said dome is constructed of materials which allow viewing of components within said sealed sample chamber and which are substantially non-porous and non-particulate generating, the materials employed further allowing for complete routine sanitization with a variety of disinfecting agents or steam sterilization procedures while offering resistance to rapid wear stemming from these sanitization procedures.

6. The remote slit impact air sampler of claim 1 wherein the exterior portion of said sample conduit, projecting through the top surface of the dome, is cylindrical in shape with the portion of said sample conduit projecting downwardly from the interior top surface of the dome being conically shaped having non-parallel sides comprising of a larger circumference at the interior top surface of the dome tapering to a smaller circumference at the bottom of said sample conduit which is roughly one half the diameter of said test plate; the interior of said sample conduit resembling a funnel, being hollow with non-parallel sides tapering from a wider circumference at the top opening to a smaller circumference at a closed bottom surface, with said sample slit cut transversely across the diameter and through the bottom surface.

7. The remote slit impact air sampler of claim 1 wherein said sample conduit is removably retained within a hole in the top surface of said dome, with said sample slit oriented in a radial position to the dome, by a laterally extending conduit flange encircling the sample conduit which retains the conduit at the interior top surface of the dome when a mounting ring is sufficiently engaged with a conduit threading which encircles the periphery of said sample conduit originating above said conduit flange and extending sufficiently from the top surface of the dome as to allow engagement with said mounting ring threading, whereby said sample conduit may be routinely removable for servicing; said sample conduit being substantially sealed to the interior and exterior top surfaces of the dome in an air tight manner by sealing means sandwiched between said conduit flange and the interior top surface of said dome and between said mounting ring and the exterior top surface of said dome.

8. A remote slit impact air sampler as described in claim 1, in combination with said test plate, said test plate consisting of a circular petri dish having an upstanding peripheral wall with said medium residing within said test plate being a microbial growth medium.

9. A remote slit impact air sampler as described in claim 1, in combination with a controller means, said controller means employed for remote operative control of the turntable drive mechanism and vacuum means.

* * * * *